(12) United States Patent
Krivokapic et al.

(10) Patent No.: US 8,750,345 B1
(45) Date of Patent: Jun. 10, 2014

(54) ASYMMETRIC UWB RADIO LINK FOR WIRELESS MEDICAL DEVICE

(75) Inventors: Ivan Krivokapic, San Diego, CA (US); Takayasu Fukuda, San Diego, CA (US)

(73) Assignee: Olympus Corporation, Tokyo (JP)

( * ) Notice: Subject to any disclaimer, the term of this patent is extended or adjusted under 35 U.S.C. 154(b) by 626 days.

(21) Appl. No.: 13/029,976

(22) Filed: Feb. 17, 2011

(51) Int. Cl.
*H04B 1/00* (2006.01)

(52) U.S. Cl.
USPC ........... 375/130; 375/219; 375/220; 375/260; 375/267

(58) Field of Classification Search
USPC .................. 375/130–153, 219, 220, 260, 267
See application file for complete search history.

(56) References Cited

U.S. PATENT DOCUMENTS

2006/0103535 A1* 5/2006 Pahlaven et al. ........... 340/572.1

* cited by examiner

*Primary Examiner* — Curtis Odom
(74) *Attorney, Agent, or Firm* — Sheppard Mullin Richter & Hampton LLP

(57) ABSTRACT

A portable medical device comprises an omnidirectional antenna; a data interface configured to receive medical video data; and a controller configured to operate in a predetermined area of reception within a health care facility with respect to a transceiver and configured to use ultra wideband communications to transmit data to the transceiver at a rate greater than about 100 MB/s with a spectral power density below a predetermined level. The transceiver is configured to provide the predetermined area of reception using a high grain antenna and is configured to use ultra wideband communications to transmit data to the first transceiver at a rate less than about 100 MB/s with a spectral power density below the predetermined level.

5 Claims, 7 Drawing Sheets

ASYMMETRIC UWB RADIO LINK FOR WIRELESS MEDICAL DEVICE

TECHNICAL FIELD

The present invention relates generally to medical devices, and more particularly, some embodiments relate to wireless communication systems for medical devices.

DESCRIPTION OF THE RELATED ART

Handheld or portable medical imaging devices such as endoscopes that provide still or video images of internal organs are widespread. Such devices often benefit from or require wireless communications technology. For example, capsule endoscopes, which require wireless communications, are swallowed by the patient and pass through the gastrointestinal tract, while handheld endoscopes benefit from the freedom and clutter reduction provided by wireless technology. Wideband communications technologies, such as those promulgated by the WiMedia consortium, are attractive for these applications because they provide for short-range high data rate applications with efficient power usage. The ultra-wideband (UWB) spectrum from 3.1 to 10.6 GHz has been allocated for low spectral density wideband transmission by the FCC. Under the WiMedia standards, this spectrum is divided in the present example into 14 bands, each with a bandwidth of 528 MHz. Each frequency band is further divided into sub-carriers, or "tones." In the WiMedia environment described herein, each band comprises 128 tones. However, other OFDM systems may employ bands with different numbers of tones. In some cases, not all tones are used for UWB transmissions. For example, some tones may be left unused to serve as guard tones, some tones may be used as pilot tones, or some tones may be nulled for a variety of reasons, such as the presence of an interfering narrowband signal on the tone or to avoid interfering with a narrowband victim on the tone.

FIG. 1 illustrates the regulatory status as of January, 2009 for UWB communication spectrum in a variety of countries as it impacts the Bands and Band Groups allocated in the WiMedia standards. Reliability is of the utmost importance for medical applications. Internationally, although Band Group I is available for use, devices using it must implement detect and avoid (DAA). DAA requires nulling tones or changing to another band when a narrowband victim signal is present. Accordingly, radio links using UWB communications in medical devices are typically required to perform robustly at the frequencies allocated for Band Groups 6 and 3 or adjacent bands. These higher frequency bands are particularly challenging due to higher path loss compared to lower frequency bands. The various regulatory bodies in charge of spectrum management have placed power spectral density limitations on transmissions in the UWB spectrum.

BRIEF SUMMARY OF EMBODIMENTS OF THE INVENTION

According to various embodiments of the invention, use of asymmetric data links and antennas provide sufficient link margins for applications that require high reliability, such as medical imaging. In particular embodiments, a data providing electronic device, such as a handheld device, transmits visual or other high rate data to a base station. The base station transmits block acknowledgement (ACK) packets and beacon packets back to the transmitting electronic device, requiring a lower data rate. Sufficient link margin for the high rate data link from the providing electronic device to the base station is maintained through the use of a high gain antenna or antenna array for reception at the base station. Because the link from the base station to the providing electronic device is at a lower rate, an omnidirectional antenna at the providing electronic device is sufficient to maintain the link.

According to an embodiment of the invention, a portable medical device, comprises an omnidirectional antenna; a data interface configured to receive medical video data; and a controller configured to operate in a predetermined area of reception within a health care facility with respect to a transceiver and configured to use ultra wideband communications to transmit data to the transceiver at a rate greater than about 100 MB/s with a spectral power density below a predetermined level; wherein the transceiver is configured to provide the predetermined area of reception using a high grain antenna and is configured use ultra wideband communications to transmit data to the first transceiver at a rate less than about 100 MB/s with a spectral power density below the predetermined level. In other embodiments, the data transmitted to the transceiver from the controller could be at rates such as 53.3, 80, 106.7, 160, 200, 320, 400, 480, 640, 800, 960, or 1024 MB/s, or other specified rates. In further embodiments, the downlink rate from the transceiver to the controller could be 53.5, 80, or 106.7 MB/s, or other specified data rates.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE
EMBODIMENTS OF THE INVENTION

Figure 1:
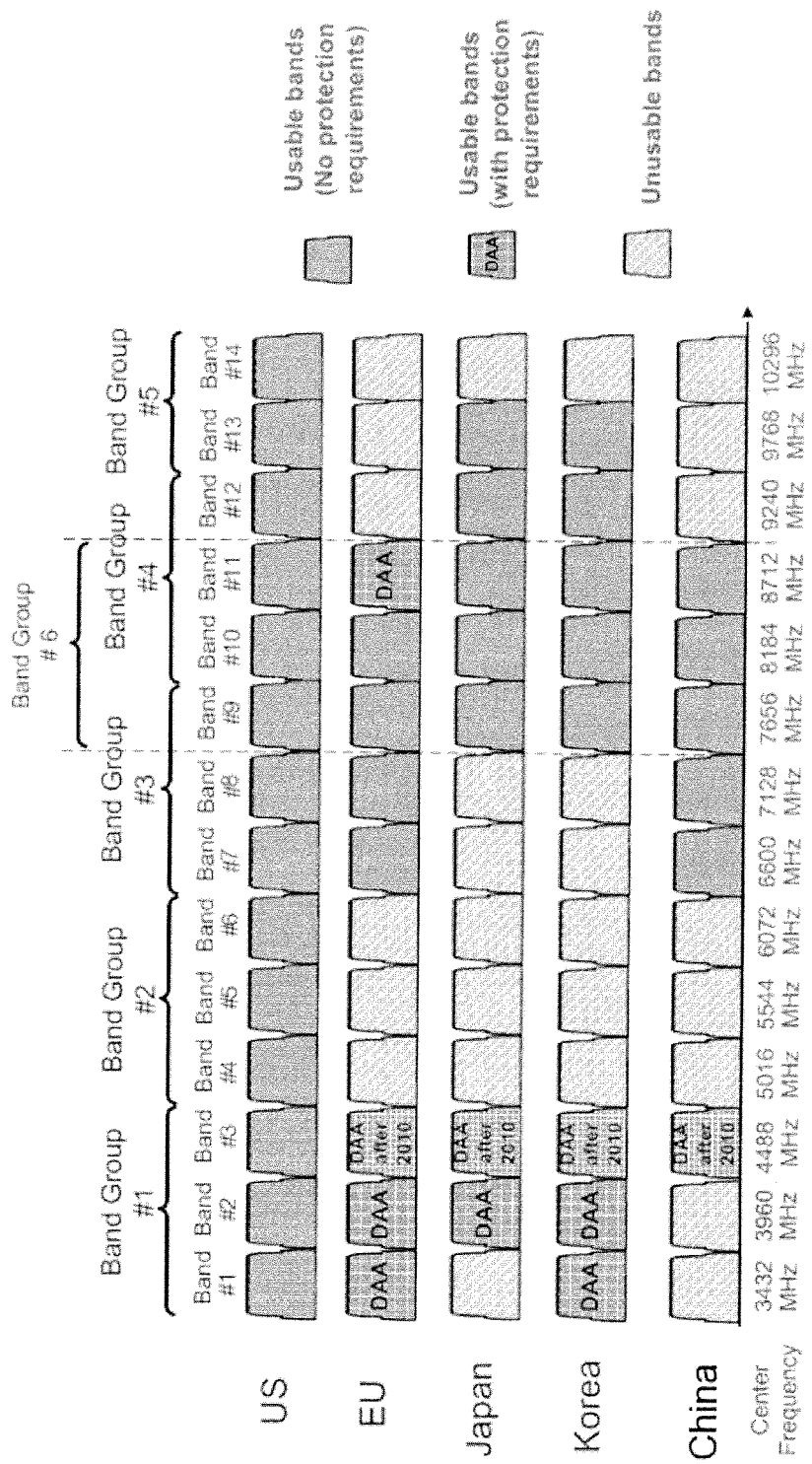
FIG. 1 illustrates the regulatory status as of January, 2009 for UWB communication spectrum in a variety of countries as it impacts the Bands and Band Groups allocated in the WiMedia standards.
Figure 2:
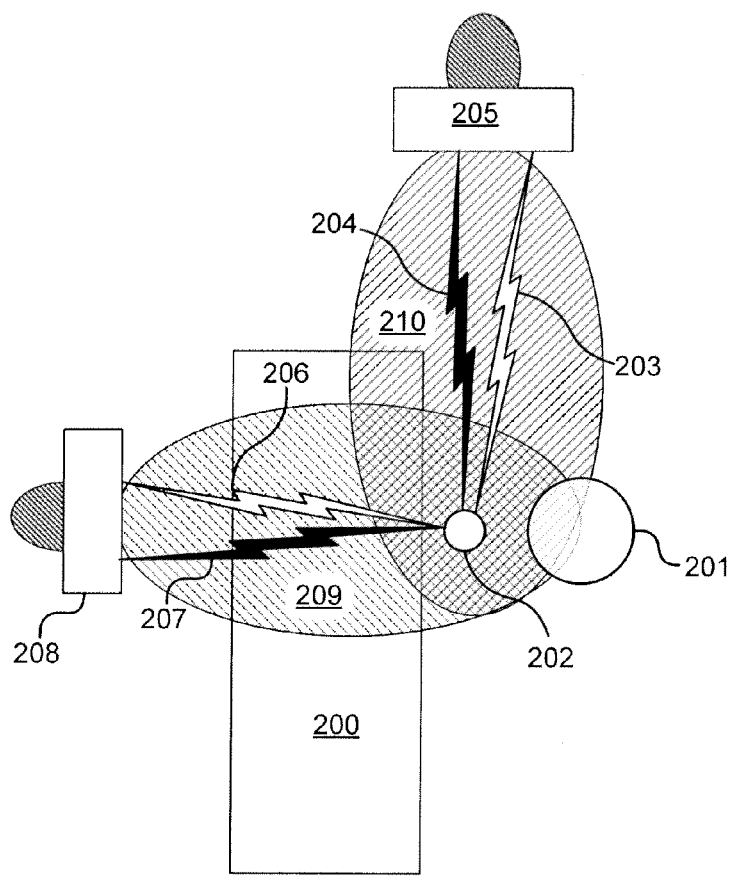
FIG. 2 illustrates an embodiment of the invention deployed in an operating room.

In conjunction with describing the invention in detail, it is useful to describe a few example environments with which the invention can be implemented. One such example is that of an operating room, or other medical environment. An embodiment of the invention deployed in such an example environment is illustrated in FIG. 2. Description in terms of these environments is provided to allow the various features and embodiments of the invention to be portrayed in the context of an exemplary application. After reading this description, it will become apparent to one of ordinary skill in the art how the invention can be implemented in different and alternative environments.

The operating room comprises an operating table 200, on which the patient lays. An operator 201, such as a medical practitioner, utilizes a data-providing or data-capture device 202 to perform a procedure on the patient. For example, in one implementation the device 202 may comprise an endoscope. A plurality of receiving devices 208 and 205 are disposed at predetermined locations within the operating room. For example, the receiving devices 208 and 205 may be embedded in or affixed to the walls of the operating room at predetermined locations. The receivers 205 and 208 in this example comprise directional antennas, such as high gain antennas or beamforming antenna arrays, that provide reception in a predetermined area of reception, 210 and 209. Although two receivers are shown in the example environment, one of ordinary skill in the art will realize that other quantities of one or more receivers can be utilized with the systems and methods described herein.

The data-providing device 202 is configured to communicate with one or both of the receivers 205 and 208 within the predetermined areas of coverage 209 and 210. The device 202 comprises an antenna that is preferably substantially omnidirectional in the plane of the operating room. In the illustrated embodiment, the device 202 uses ultrawideband communications, for example according to the WiMedia communication standard, or other communications protocol, to communicate establish one or more outgoing links 203 and 206 and incoming links 204 and 207 with one or more of the receivers 205 and 208. When used by operator 201 the device 202 generates visual or other high rate data, for example at a rate of about 200 MB/s, and transmits the data to receiver 205 or 208 via outgoing link 203 or 206. The receivers in turn generate beaconing data and ACK data that is transmitted to the device 202 at a substantially lower rate, for example at a rate of about 53 MB/s, via incoming links 204 and 207. In various embodiments, the down link, having a lower data rate for beaconing and ACK has a high processing gain, and so is not critical to performance. Rather, achieving a quality uplink is important from an image or other data quality perspective.

In various embodiments, a predetermined minimal link margin is established for the communications system. In particular embodiments, particularly embodiments where the data providing device will be handheld or portable, the minimal link margin is 6 dB, this link margin reduces error beyond the minimal recommend link margin for WiMedia applications. In other embodiments, this link margin may be relaxed, for example 3 dB may be used in some applications, such as WiMedia applications to achieve an error flow of 0.01%. In other embodiments, these link margin requirements may be modified. For example, in satellite links margin could be less then 1 dB due to very predictable link performances. As discussed above, embodiments of the invention operate under predetermined spectral density requirements, such as a maximum spectral density of −41.25 dBm/MHz in 503 MHz bands. Accordingly, the receivers 205 and 208 are configured to provide a sufficient receiver sensitivity in the reception areas 208 and 210 to achieve the predetermined minimal link margin.

Figure 3A:
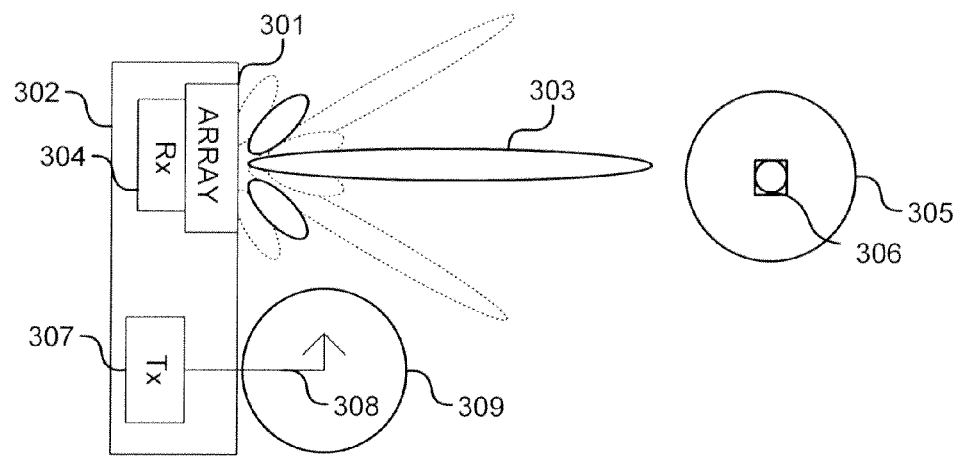
FIG. 3A illustrates embodiments of the invention utilizing beamforming to provide the predetermined reception area having the predetermined link margin.

FIG. 3A illustrates example embodiments of the invention utilizing beamforming to provide the predetermined reception area having the predetermined link margin. In the illustrated embodiment, a wireless device 306 establishes a wireless communications link using a wideband communications protocol, such as the WiMedia communications protocol, with a base station 302. The device 306 transmits data to the base station 302 at a predetermined data rate and a predetermined maximum power spectral density. The device 306 comprises an omnidirectional or planar omnidirectional antenna that has an omnidirectional radiation pattern 305. Accordingly, as the device 306 is moved or re-oriented, the uplink to the base station 302 is maintained while the device 306 is in the predetermined reception area.

The base station 302 comprises a receiver subsystem 304 comprising an antenna array 301 or other fixed or adaptive beam steerable system. For example a phased array antenna can be implemented as antenna array 301 to provide electronic beam steering. Examples can include linear arrays or planar arrays to allow the beam to be steered utilizing analog or digital beamforming The base station 302 implements beam forming using the antenna array 301 to direct the radiation pattern toward a predetermined reception area. Accordingly, a reception pattern (for example, pattern 303) having sufficient antenna gain within the predetermined reception area can be selected to improve system performance. Preferably, the system is configured such that the beam forming is used to maintain the predetermined minimal link margin with the device 306.

In various embodiments, techniques can be implemented to allow the selection of the appropriate radiation pattern or beam steering to optimize system performance. For example, upon setup of the system in an operational configuration with devices 306 and 302 in their operational positions, the receive array 301 can be configured to scan through the available radiation patterns to select the one with the best performance (e.g., the one that yields the best Signal-to-Noise Ratio (SNR)). As another example, when the base station 302 is positioned in its environment, the pattern can be user selected to direct the beam toward a predetermined location, such as the anticipated location of device 306. For example, in terms of the example environment, where a base station 302 or receiver 205, 208 is mounted on a wall of the operating room, an antenna pattern directed toward the operating table or other location where the transmitter 306 or data-providing device 202 is to be used. Additionally, a hybrid approach can be utilized in which a general area is selected in which to direct the beam, and electronic methods are used to fine-tune the beam steering to improve signal reception.

Because in some environments, transmitting device 306 may move relative to receiving device 302, the beam steering can be configured to be dynamic beam steering, for example, allowing the system to scan through alternative patterns should performance degrade. For example, should the SNR fall below a predetermined threshold.

The receiver 302 further comprises a transmitter subsystem 307. In the illustrated embodiment the transmitter subsystem comprises an omnidirectional antenna 308 having a circular radiation pattern 309. The base station transmits beaconing data and ACK data to the device 306, which the device receives using the omnidirectional antenna. In the illustrated embodiment, the base station 302 operates under the same power spectral density requirements as the device 306. The predetermined link margin is maintained because the base station 302 is limited to a substantially lower data rate required for transmission of the beacon and ACK information.

Figure 3B:
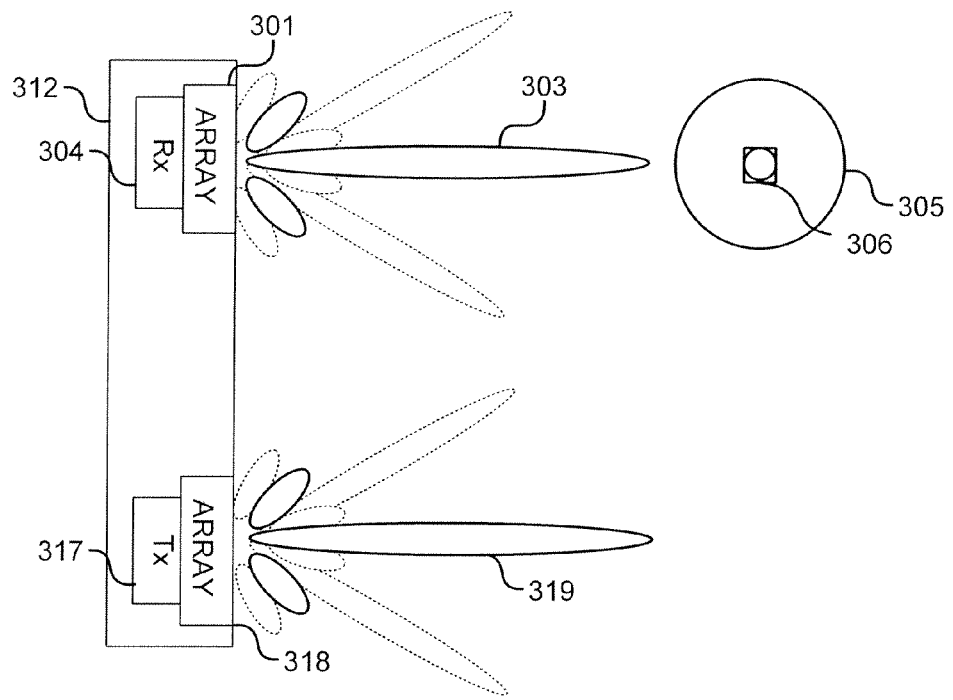
FIG. 3B illustrates embodiments of the invention utilizing beamforming to provide the predetermined reception area and for transmission to the electronic device.

FIG. 3B illustrates example embodiments of the invention utilizing beamforming to provide the predetermined reception area and for transmission to the electronic device. In the illustrated embodiment, like reference numbers refer to like elements as described above with respect to FIG. 3A. In this embodiment, the base station 312 comprises a transmission subsystem 317 comprising an antenna array 318 to implement beamforming to transmit the low data rate downlink information to the device 306 with a radiation pattern 319. Additionally, in some embodiments, antenna arrays 318 and 301 may be the same antennas. Although the base station 312 is subject to the predetermined maximum power spectral density, the use of beamforming 319 may provide other benefits, such as reduction of interference to adjacent devices or reduction of multipath effects.

Figure 4A:
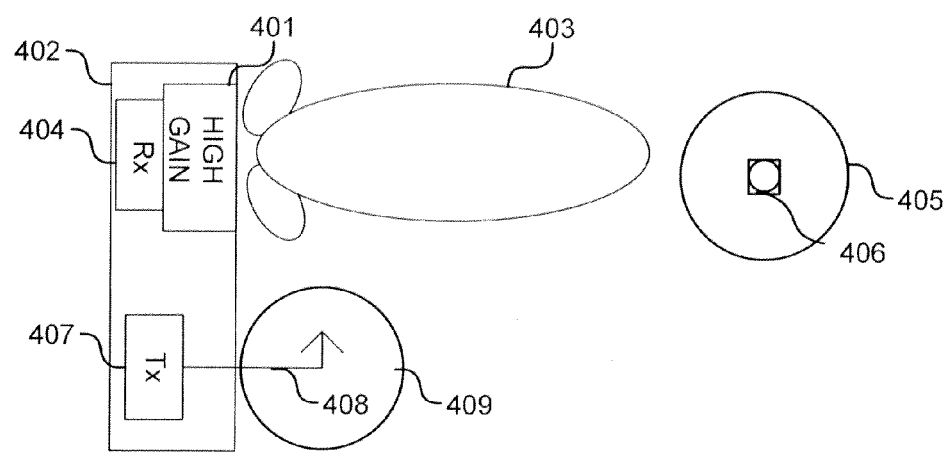
FIG. 4A illustrates embodiments of the invention utilizing a directional antenna to provide the predetermined reception area having the predetermined link margin.

FIG. 4A illustrates example embodiments of the invention utilizing a directional antenna to provide the predetermined reception area to accommodate the predetermined link margin. In the illustrated embodiment, a wireless device 406 establishes a wireless communications link using a wideband communications protocol, such as the WiMedia communications protocol, with a base station 402. The device 406 transmits data to the base station 402 at a predetermined data rate and a predetermined maximum power spectral density. The device 406 comprises an omnidirectional or planar omnidirectional antenna that has an omnidirectional radiation pattern 405. Accordingly, as the device 406 is moved or re-oriented, the uplink to the base station 402 is maintained while the device 406 is in the predetermined reception area. The base station 402 comprises a receiver subsystem 404 comprising a high gain antenna 401.

The base station 403 uses the high gain antenna 401 to provide a predetermined reception area with a reception pattern 303 having sufficient antenna gain within the predetermined reception area to maintain the predetermined minimal link margin with the device 406. For example, a directional antenna with a relatively narrow beam width can be implemented as high gain antenna 401. Using an antenna with a directional or focused beam allows the antenna's reception area to be targeted to the device 406. Accordingly, link margins can be improved using a properly oriented high-gain antenna as compared to an omni-directional antenna.

The receiver 402 further comprises a transmitter subsystem 407. In the illustrated embodiment the transmitter subsystem comprises an omnidirectional antenna 408 having a circular radiation pattern 409. The base station transmits beaconing data and ACK data to the device 406, which the device receives using the omnidirectional antenna. In the illustrated embodiment, the base station 402 operates under the same power spectral density requirements as the device 406. The predetermined link margin is maintained because the base station 402 is limited to a substantially lower data rate required for transmission of the beacon and ACK information.

Figure 4B:
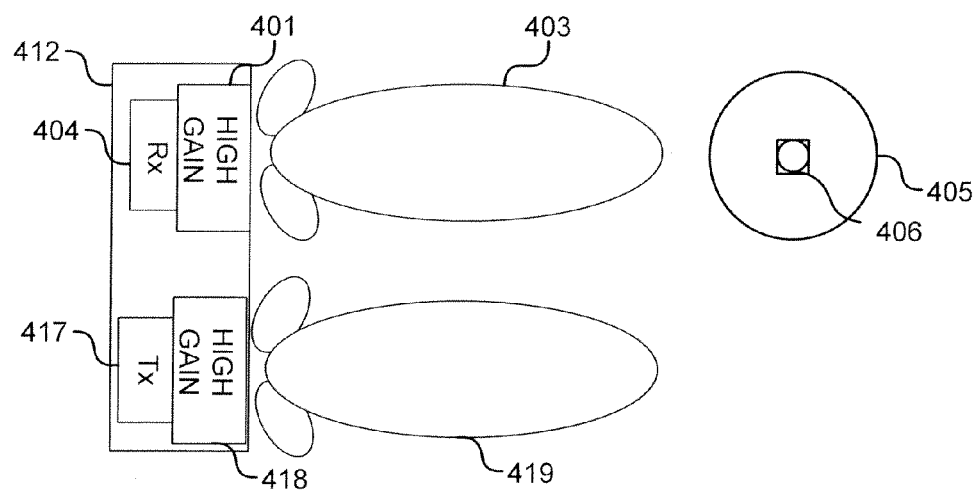
FIG. 4B illustrates embodiments of the invention utilizing beamforming to provide the predetermined reception area and for transmission to the electronic device.

FIG. 4B illustrates example embodiments of the invention utilizing beamforming to provide the predetermined reception area and for transmission to the electronic device. In the illustrated embodiment, like reference numbers refer to like elements as described above with respect to FIG. 4A. In this embodiment, the base station 412 comprises a transmission subsystem 417 comprising a high gain antenna 418 that provides directional antenna gain with a radiation pattern 419 to transmit information to the device 406. Additionally, in some embodiments, high gain antennas 418 and 401 may be the same antennas. Although the base station 412 is subject to the predetermined maximum power spectral density, the use of the directional antenna pattern 419 may provide other benefits, such as reduction of interference to adjacent devices or reduction of multipath effects.

Figure 5A:
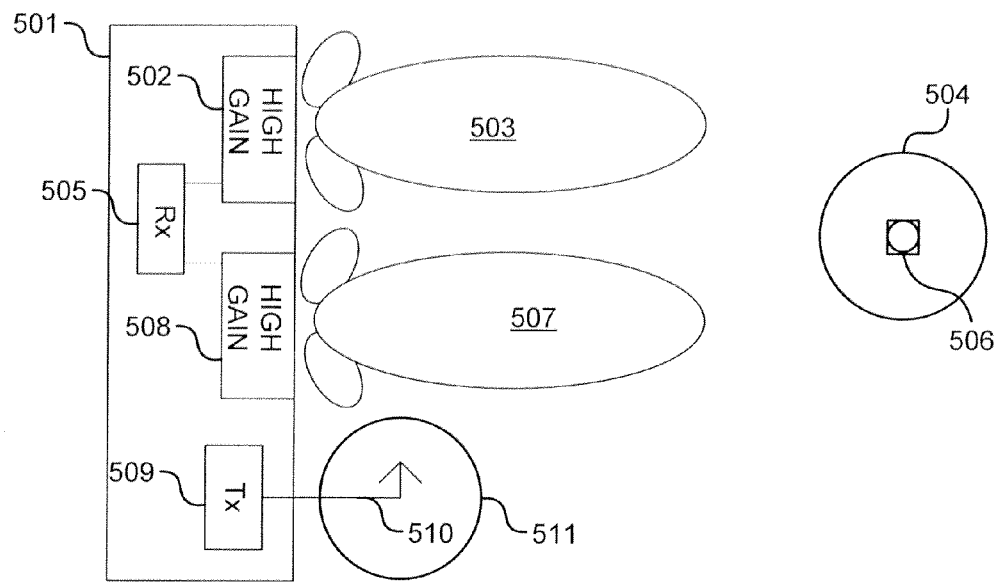
FIG. 5A illustrates an embodiment utilizing high gain directional antennas and receiver maximum ratio combining to provide the predetermined reception area for the electronic device.

FIG. 5A illustrates an embodiment utilizing high gain directional antennas and receiver diversity to provide the predetermined reception area for the electronic device. In the illustrated embodiment, a wireless device 506 establishes a wireless communications link having an uplink component and a downlink component with a receiver or base station 501. In some embodiment, the device 506 utilizes an omnidirectional antenna having a radiation pattern 504 for transmission and reception. The wireless communication link is established using a wideband communications protocol, such as the WiMedia communications protocol. The devices operate under predetermined maximum power spectral density requirements. The device 506 cannot increase its transmission power above this predetermined limit. To achieve a predetermined minimum link margin on the uplink, the base station 501 provides a predetermined reception area having sufficient antenna gain to allow the uplink from the device 506 to maintain the predetermined minimum link margin. In this embodiment, the predetermined reception area is provided by the receiver subsystem 505 of the base station 501. The receiver subsystem 505 comprises a plurality of high gain antennas 502 and 508 having radiation patterns 503 and 507, respectively. The receiver subsystem is configured to implement antenna diversity, such as maximum ratio combining (MRC) to provide the predetermined area of reception. Using two or more antennas can improve the performance of the link in terms of signal strength and reliability, as the multiple antennas provide multiple observations of the same signal. The base station 501 further comprises a transmitter subsystem 509 comprising an omnidirectional antenna 510 having a radiation pattern 511. Because the downlink to the device 506 has a substantially lower data rate than the uplink, the device's 506 omnidirectional antenna is sufficient to maintain the downlink with the predetermined minimum link margin.

Figure 5B:
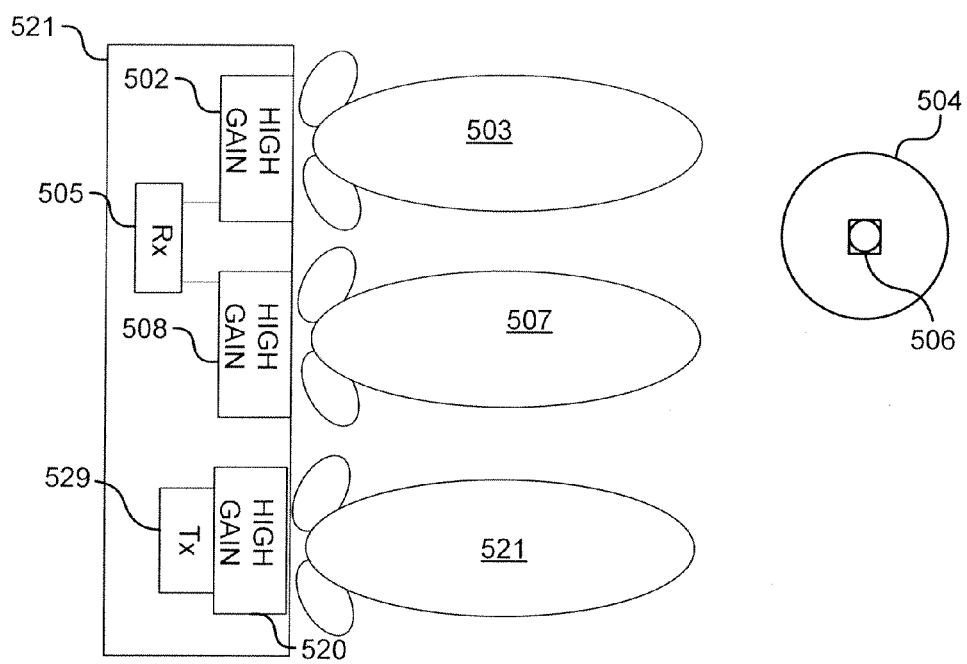
FIG. 5B illustrates embodiments of the invention utilizing beamforming to provide the predetermined reception area and for transmission to the electronic device.

FIG. 5B illustrates embodiments of the invention utilizing beamforming to provide the predetermined reception area and for transmission to the electronic device. In the illustrated embodiment, like reference numbers refer to like elements as described above with respect to FIG. 5A. In this embodiment, the base station 521 comprises a transmission subsystem 529 comprising a high gain antenna 520 having a radiation pattern 521 to transmit information to the device 506. Although the base station 521 is subject to the predetermined maximum power spectral density, the use of the directional antenna pattern 521 may provide other benefits, such as reduction of interference to adjacent devices or reduction of multipath effects.

Figure 6A:
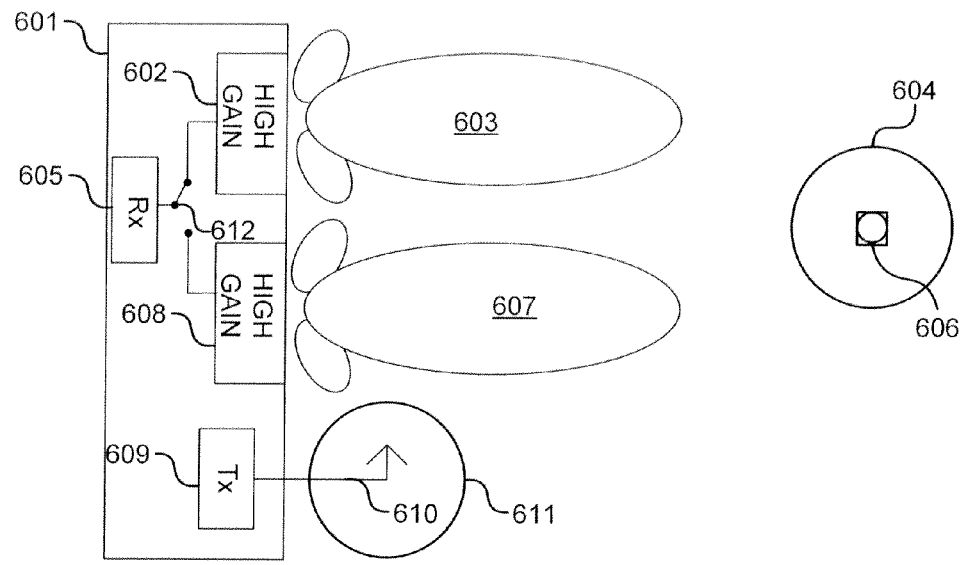
FIG. 6A illustrates an embodiment utilizing high gain directional antennas and spatial diversity to provide the predetermined reception area for the electronic device.

FIG. 6A illustrates an embodiment utilizing high gain directional antennas and spatial diversity to provide the predetermined reception area for the electronic device. In the illustrated embodiment, a wireless device 306 establishes a wireless communications link having an uplink component and a downlink component with a receiver or base station 601. In some embodiment, the device 606 utilizes an omnidirectional antenna having a radiation pattern 604 for transmission and reception. The wireless communication link is established using a wideband communications protocol, such as the WiMedia communications protocol. The devices operate under predetermined maximum power spectral density requirements. The device 606 cannot increase its transmission power above this predetermined limit. To achieve a predetermined minimum link margin on the uplink, the base station 601 provides a predetermined reception area having sufficient antenna gain to allow the uplink from the device 606 to maintain the predetermined minimum link margin. In this embodiment, the predetermined reception area is provided by the receiver subsystem 605 of the base station 501. The receiver subsystem 605 comprises a plurality of physically spaced apart high gain antennas 602 and 608 having radiation patterns 603 and 607, respectively. The receiver subsystem is configured to implement spatial diversity using switch 612 to switchably connect to either antenna 602 or antenna 608 according to whichever antenna provides superior reception for the device 606 at its present location. The substation further comprises a transmitter subsystem 609 comprising an omnidirectional antenna 610 having a radiation pattern 611. Because the downlink to the device 606 has a substantially lower data rate than the uplink, the device's 606 omnidirectional antenna is sufficient to maintain the downlink with the predetermined minimum link margin.

Figure 6B:
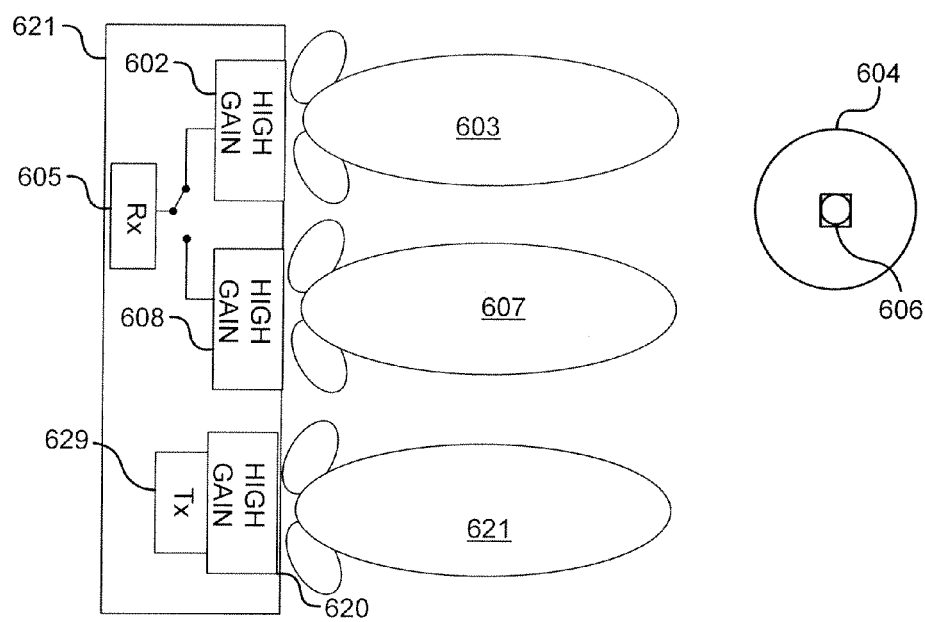
FIG. 6B illustrates embodiments of the invention utilizing beamforming to provide the predetermined reception area and for transmission to the electronic device.

FIG. 6B illustrates embodiments of the invention utilizing beamforming to provide the predetermined reception area and for transmission to the electronic device. In the illustrated embodiment, like reference numbers refer to like elements as described above with respect to FIG. 6A. In this embodiment, the base station 621 comprises a transmission subsystem 629 comprising a high gain antenna 620 having a radiation pattern 621 to transmit information to the device 506. Although the base station 621 is subject to the predetermined maximum power spectral density, the use of the directional antenna pattern 621 may provide other benefits, such as reduction of interference to adjacent devices or reduction of multipath effects.

Figure 7:
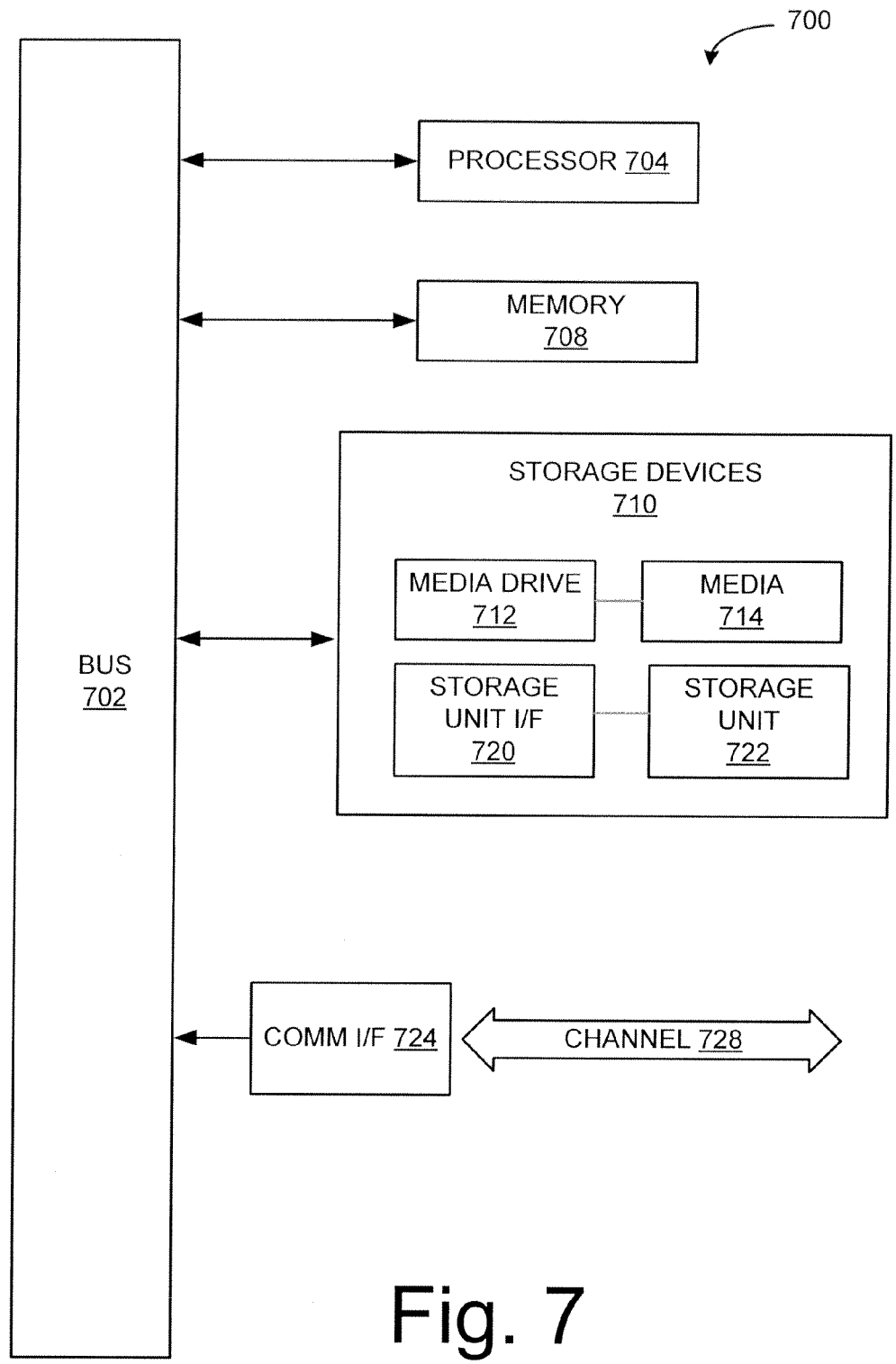
FIG. 7 illustrates an example computing module that may be used in implementing various features of embodiments of the invention.

In various embodiments, electronic devices implemented in accordance with embodiments of the invention may utilize various modules. As used herein, the term module might describe a given unit of functionality that can be performed in accordance with one or more embodiments of the present invention. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the invention are implemented in whole or in part using software, in one embodiment, these software elements can be implemented to operate with a computing or processing module capable of carrying out the functionality described with respect thereto. One such example computing module is shown in FIG. 7. Various embodiments are described in terms of this example-computing module 700. After reading this description, it will become apparent to a person skilled in the relevant art how to implement the invention using other computing modules or architectures.

Referring now to FIG. 7, computing module 700 may represent, for example, computing or processing capabilities found within desktop, laptop and notebook computers; handheld computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 700 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 700 might include, for example, one or more processors, controllers, control modules, or other processing devices, such as a processor 704. Processor 704 might be implemented using a general-purpose or special-purpose processing engine such as, for example, a microprocessor, controller, or other control logic. In the illustrated example, processor 704 is connected to a bus 702, although any communication medium can be used to facilitate interaction with other components of computing module 700 or to communicate externally.

Computing module 700 might also include one or more memory modules, simply referred to herein as main memory 708. For example, preferably random access memory (RAM) or other dynamic memory, might be used for storing information and instructions to be executed by processor 704. Main memory 708 might also be used for storing temporary variables or other intermediate information during execution of instructions to be executed by processor 704. Computing module 700 might likewise include a read only memory ("ROM") or other static storage device coupled to bus 702 for storing static information and instructions for processor 704.

The computing module 700 might also include one or more various forms of information storage mechanism 710, which might include, for example, a media drive 712 and a storage unit interface 720. The media drive 712 might include a drive or other mechanism to support fixed or removable storage media 714. For example, a hard disk drive, a floppy disk drive, a magnetic tape drive, an optical disk drive, a CD or DVD drive (R or RW), or other removable or fixed media drive might be provided. Accordingly, storage media 714 might include, for example, a hard disk, a floppy disk, magnetic tape, cartridge, optical disk, a CD or DVD, or other fixed or removable medium that is read by, written to or accessed by media drive 712. As these examples illustrate, the storage media 714 can include a computer usable storage medium having stored therein computer software or data.

In alternative embodiments, information storage mechanism 710 might include other similar instrumentalities for allowing computer programs or other instructions or data to be loaded into computing module 700. Such instrumentalities might include, for example, a fixed or removable storage unit 722 and an interface 720. Examples of such storage units 722 and interfaces 720 can include a program cartridge and cartridge interface, a removable memory (for example, a flash memory or other removable memory module) and memory slot, a PCMCIA slot and card, and other fixed or removable storage units 722 and interfaces 720 that allow software and data to be transferred from the storage unit 722 to computing module 700.

Computing module 700 might also include a communications interface 724. Communications interface 724 might be used to allow software and data to be transferred between computing module 700 and external devices. Examples of communications interface 724 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 724 might typically be carried on signals, which can be electronic, electromagnetic (which includes optical) or other signals capable of being exchanged by a given communications interface 724. These signals might be provided to communications interface 724 via a channel 728. This channel 728 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 708, storage unit 720, media 714, and channel 728. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 700 to perform features or functions of the present invention as discussed herein.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A ultra wideband radio communication system, comprising:
   a first transceiver comprising an omnidirectional antenna; and
   a second transceiver comprising a high gain antenna or an antenna array;
   wherein the first transceiver is configured to operate in a predetermined area of reception with respect to the second transceiver and is configured to use ultra wideband communications to transmit data to the second transceiver at a rate greater than about 100 MB/s with a spectral power density below a predetermined level; and
   wherein the second transceiver is configured to provide the predetermined area of reception using the high grain antenna and is configured use ultra wideband communications to transmit data to the first transceiver at a rate less than about 100 MB/s with a spectral power density below the predetermined level.

2. The ultra wideband radio communication system of claim 1, wherein the second transceiver comprises a plurality of high gain antennas.

3. The ultra wideband radio communication system of claim 2, wherein the second transceiver is configured to implement maximum ratio combining using the plurality of high gain antennas to provide the predetermined area of reception.

4. The ultra wideband radio communication system of claim 2, wherein the second transceiver is configured to implement spatial diversity using the plurality of high gain antennas to provide the predetermined area of reception.

5. The ultra wideband radio communication system of claim 1, wherein the data transmitted to the second transceiver comprises video data and the data transmitted to the first transceiver comprises block acknowledgement data.

* * * * *

UNITED STATES PATENT AND TRADEMARK OFFICE
CERTIFICATE OF CORRECTION

| | |
|---|---|
| PATENT NO. | : 8,750,345 B1 |
| APPLICATION NO. | : 13/029976 |
| DATED | : June 10, 2014 |
| INVENTOR(S) | : Ivan Krivokapic et al. |

It is certified that error appears in the above-identified patent and that said Letters Patent is hereby corrected as shown below:

In the Claims

Claim 1, Column 11, line 2, "A ultra" should read --An ultra--

Claim 1, Column 11, line 16, "configured use" should read --configured to use--

Signed and Sealed this
Twelfth Day of August, 2014

Michelle K. Lee
*Deputy Director of the United States Patent and Trademark Office*